United States Patent [19]

Martin et al.

[11] Patent Number: 5,334,752
[45] Date of Patent: Aug. 2, 1994

[54] CYCLOBUTABENZENE MONOMERS

[75] Inventors: David C. Martin; Jeffrey S. Moore, both of Ann Arbor; Larry J. Markoski, Wayland, all of Mich.; Kenneth A. Walker, Urbana, Ill.

[73] Assignee: The Board of Regents acting for and on behalf of University of Michigan, Ann Arbor, Mich.

[21] Appl. No.: 907,430

[22] Filed: Jul. 1, 1992

[51] Int. Cl.$^5$ .......................................... C07C 205/12
[52] U.S. Cl. ........................... 560/360; 562/488; 562/855; 564/427; 564/428; 568/327; 568/738
[58] Field of Search ............... 560/360; 562/488, 855; 564/427, 428; 508/734, 327

[56] References Cited

U.S. PATENT DOCUMENTS

| | | | |
|---|---|---|---|
| 3,105,845 | 10/1963 | Fetterly et al. | 560/360 |
| 3,180,883 | 4/1965 | Case | 560/360 |
| 3,637,740 | 1/1972 | Sarges | 564/428 |
| 4,570,011 | 2/1986 | So | 562/488 |

OTHER PUBLICATIONS

Markoski et al, Chem. Mater., vol. 5(3), pp. 248–250 (1993).
Walker et al, Synthesis, vol. 12, pp. 1265–1268 (1992).
Kanao et al, Tet. Letters, vol. 24, pp. 1727–1730 (1983).
Oda et al, Chem. Lett., pp. 37–38 (1981).
Watabe et al, Chem. Lett, pp. 1791–1794 (1984).
Iyoda et al, Chem. Lett, pp. 2113–2116 (1986).

Primary Examiner—James H. Reamer
Attorney, Agent, or Firm—Rohm & Monsanto

[57] ABSTRACT

Novel difunctionalized cyclobutabenzene monomers of the general formula:

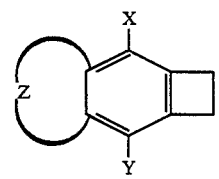

wherein Z can be hydrogens or a cyclobutane ring; and X and Y are carboxyl, amino, alcohol, isocyanate, acid halide, or bis-acyl fluoride groups. In a particularly preferred embodiment, the cyclobutabenzene derivative is 1,2-dihydrocyclobutabenzene-3,6-carboxylic acid. The difunctionalized cyclobutabenzene monomer can form part of a polymer backbone chain, but has an additional functionality, the butane ring, which can be easily opened to produce strong, covalent bond crosslinking between polymer chains. The crosslinking can be induced simply by heating the polymer to a temperature in excess of 300° C.

6 Claims, 5 Drawing Sheets

CYCLOBUTABENZENE MONOMERS

BACKGROUND OF THE INVENTION

This invention relates generally to novel cyclobutabenzene derivatives, and more particularly, to acid or acid halide difunctionalized cyclobutabenzene derivatives which can be incorporated into any polymeric backbone structure as a substitute for, or in conjunction with, terephthalic acid or its acid chloride analog.

Recently, much effort has been expended toward producing high performance engineering thermoplastics with improved polymer microstructure in order to achieve specific desired polymer properties, such as strength, stiffness, long term dimensional stability, or acid/high temperature resistance. Some of this effort has been directed to incorporating cyclobutabenzene groups into known polymers.

The cyclobutabenzenes are useful because of a crosslinking reaction which can be thermally triggered resulting in ring-opening of cyclobutabenzene (BCB) to form the highly reactive o-quinodimethane intermediate at temperatures above 300° C.:

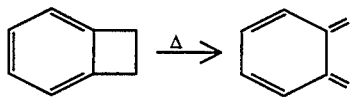

The o-quinodimethane intermediate is sufficiently reactive to homopolymerize through an addition reaction or by Diels-Alder dimerization. In either case, crosslinking should take place with little or no mass loss as the cyclobutane ring unfurls.

Previous use of the BCB functionality in polymer chemistry has been limited to structoterminal prepolymers (i.e., oligomers encapped with BCB). When the BCB functionality is used as an end-group in a polymer molecule, crosslinking occurs only at the end of the polymer molecules, and therefore, the degree of crosslinking is directly related to the molecular weight. When BCB functionalities are placed as a reactive pendant groups along the polymer backbone, the degree of crosslinking can be controlled. However, the resulting crosslinks are flexible and are not very ordered. This can lead to a lower modulus and disruption of crystallinity in the polymer, and hence, lower performance of polymer properties. Moreover, in both cases, the crosslinking function must be performed after polymerization is complete.

These approaches, therefore, suffer from limited processability and limited ability to vary crosslink density. There is, thus, a need for a structopendant crosslinking group (i.e., a crosslinking group placed directly in the backbone of the polymer as a monomeric unit), such that the reactive crosslinking functionality remains intact for secondary polymerization. This would permit greater control of the extent of crosslinking to achieve high performance polymers having particular desired properties. There is a further need for a structopendant crosslinking group which can be activated for crosslinking at any desired time during the processing, including subsequent to fiber formation, casting, or molding.

In all of the structoterminal prepolymers mentioned above, the aromatic BCB ring was simply monofunctionalized at the 4 position (the product accessible through electrophilic aromatic substitution). There is a need in the art for difunctionalized cyclobutabenzene derivatives which can be used as structopendant crosslinking groups. One obstacle encountered in incorporating the BCB functionality into the backbone of a polymer has been the difficulty in producing regioselective difunctionalization of the cyclobutabenzene unit. There is, therefore, a need for a method for regioselectively introducing a difunctionality onto the 3 and 6 positions of cyclobutabenzene.

Terephthalic acid (TA) is a difunctionalized monomer which is widely used in the production of high-performance aromatic polymers such as Poly{(benzo-[1,2-d;4,5-d']-bisoxazole-2,6-diyl)-1,4-phenylene} (PBZO), Poly{(benzo-[1,2-d;4,5-d']-bisthiazole-2,6-diyl)-1,4-phenylene} (PBZT), Poly(p-phenylene terephthalamide) (PPTA or Kevlar®, a trademark of Dupont Chemical Company, Wilmington, Del.), and Poly(ethylene terephthalate) (PET). PPTA, PBZO, and PBZT, for example, are present state-of-the-art polymer materials for lightweight structural applications. Although these materials are strong and stiff, they are disadvantageously relatively weak in compression. The compression failure occurs by strain localization into well-defined kink bands. Detailed structural investigation of the kink bands using High Resolution Electron Microscopy revealed that both chain slip and chain bending or breaking are involved in this deformation mode.

PPTA, PBZO and PBZT are all bonded laterally in the solid state by weak secondary forces. There is a need in the art for a means of providing strong, covalent lateral crosslinks between the polymer molecules in these high-performance polymers to further improve their mechanical properties. There is, thus, a need in the art for an analog of TA which has an additional functionality having the ability to produce such strong, covalent crosslinks between polymer chains. There is a further need in the art for an analog of TA which can advantageously be substituted therefore to improve polymer properties without modifying existing processes.

It is, therefore, an object of this invention to provide difunctionalized cyclobutabenzene monomers and methods of making same.

It is another object of the invention to provide difunctionalized cyclobutabenzene monomers which can be substituted for existing corresponding monomers in existing polymers without substantially modifying the existing processes.

It is also an object of this invention to provide difunctionalized cyclobutabenzene monomers for controlled incorporation of a cyclobutane functionality into a polymer backbone to yield polymers of improved mechanical compressive strength and well as other improved properties.

It is still a further object of the invention to provide a method for regioselectively introducing a difunctionality onto the 3 and 6 positions of a cyclobutabenzene.

SUMMARY OF THE INVENTION

The foregoing and other objects are achieved by this invention which provides difunctionalized cyclobutabenzene monomers having a disubstituted benzene ring to which one or more unsubstituted cyclobutane rings are fused. The difunctionalized cyclobutabenzene monomers have the general formula:

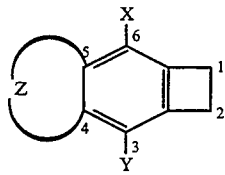

where Z is hydrogens or a cyclobutane ting. The X and Y substituents, which may be the same or different, are —COOH, —NH₂, —OH, —COCl, —NCO, or bis acyl fluoride. The ring positions have been numbered for nomenclature purposes.

The X/Y substituents are chosen so that the cyclobutabenzene participates as a monomer in a primary polymerization reaction via the substituent functionalities so that the cyclobutabenzene is a component of the polymeric backbone. Thus, the cyclobutane functionality is available for secondary polymerization, or cross-linking, to produce strong, covalent bonds between polymer chains.

In particular preferred embodiments, the cyclobutabenzene derivatives are 1,2-dihydrocyclobutabenzene3,6-carboxylic acid; 1,2-dihydrocyclobutabenzene-3,6-diamine; 1,2-dihydrocyclobutabenzene-3,6-isocyanate; 1,2-dihydrocyclobutabenzene-3,6-acid halide; and 3,6-hydroxy-1,2-dihydrocyclobutabenzene.

In further embodiments, resins are provided from polymerization of the novel monomers with copolymers which are capable of reacting with the X/Y functionalities of the cyclobutabenzene monomer. Heating the resins, preferably to a temperature in excess of 300° C., at any time during processing, causes crosslinking by disrupting the butane ring.

In an illustrative embodiment, the cyclobutabenzene diacid halide monomer of the present invention is condensed with a diamine which contains at least two carbon atoms between the amino groups to form a polyamide. In another illustrative embodiment, the cyclobutabenzene diisocyanate may be polymerized with a diol of similar structure to the aforementioned diamine to form a polyurethane. These are but two examples of the numerous polymers that can be synthesized using one of more of the cyclobutabenzene derivatives of the present invention.

In a process aspect of the invention, a difunctionalized cyclobutabenzene derivative can be made by:

a) convening cyclobutabenzene to 3,6-ditrimethylsilylcyclobutacyclohexadiene by reductive silylation of as first described by Kundig, et al.;

b) aromatizing 3,6-ditrimethylsilylcyclobutacyclohexadiene to fully saturate the cyclohexadiene ring to form 3,6-ditrimethylsilyl-1,2-dihydrocyclobutabenzene;

c) replacing the trimethylsilyl functionality with a halide to form 3,6-dibromo-1,2-dihydrocyclobutabenzene; and d) converting the dihalide to a 1,2-dihydrocyclobutabenzene-3,6-carboxylate via a palladium catalyzed carbonylation reaction and subsequent hydrolysis of the diester to form 1,2-dihydrocyclobutabenzene-3,6-carboxylic acid.

In an alternative embodiment, the dihalide can be converted to 1,2-dihydrocyclobutabenzene-3,6-3,6-carboxylic acid by a Grignard reaction.

In a further process embodiment, 1,2-dihydrocyclobutabenzene-3,6-carboxylic acid can be converted to the corresponding acid halide using thionyl chloride to form 1,2-dihydrocyclobutabenzene-3,6-acid chloride.

BRIEF DESCRIPTION OF THE DRAWINGS

Comprehension of the invention is facilitated by reading the following detailed description, in conjunction with the annexed drawing, in which.

DETAILED DESCRIPTION OF PREFERRED EMBODIMENTS

The following specific examples relate to specific embodiments of the difunctionalized cyclobutabenzene analogs of the present invention, and include illustrative methods for synthesizing same.

In a preferred embodiment, the difunctionalized cyclobutabenzene monomer is a derivative of terephthalic acid (TA), specifically, 1,2-dihydrocyclobutabenzene-3,6-carboxylic acid (herein designated as XTA):

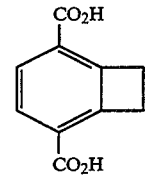

Although XTA is similar in structure to TA, it has an additional functionality, the butane ring, which can be easily opened to produce crosslinking between polymer chains. The crosslinking reaction can be induced simply by heating the polymer to a temperature in excess of 300° C.

In certain preferred embodiments, XTA can be used as a monomer or as a comonomer with TA or its acid chloride analog. By varying the amount of XTA:TA in a polymer reaction, it is possible to systematically tailor the properties of the system to achieve mechanical properties not achievable with either XTA or TA alone. For example, a 1:1 mixture of XTA and TA would yield approximately half the number of BCB groups that the homopolymerization reaction would yield, and thus, would decrease the extent of crosslinking by a factor of two. The extent of crosslinking can be easily controlled by adjusting the ratio of monomers used in the polymerization reaction. Therefore it is possible to significantly alter the mechanical strengths of oriented polymer fibers in compression.

Other structures specifically within the contemplation of the invention include:

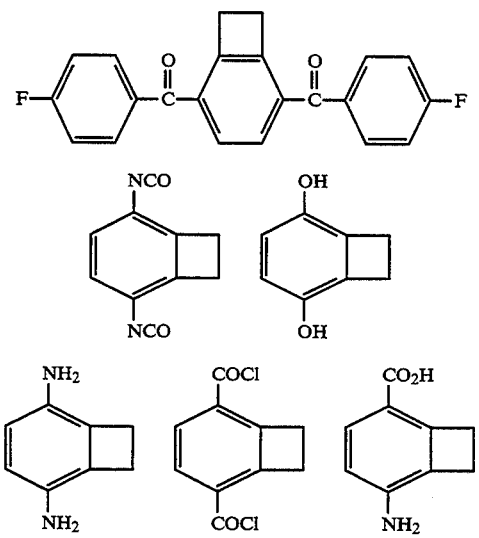

In further embodiments, Z comprises a second cyclobutane ring:

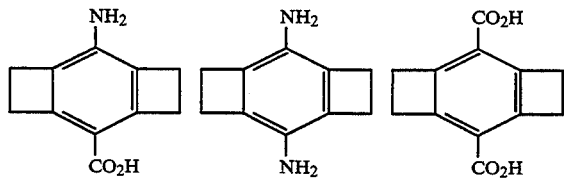

Structures including the second cyclobutane ring increase the possible number of crosslinks by a factor of two and are advantageous for producing a high degree of crosslinking.

Figure 1:
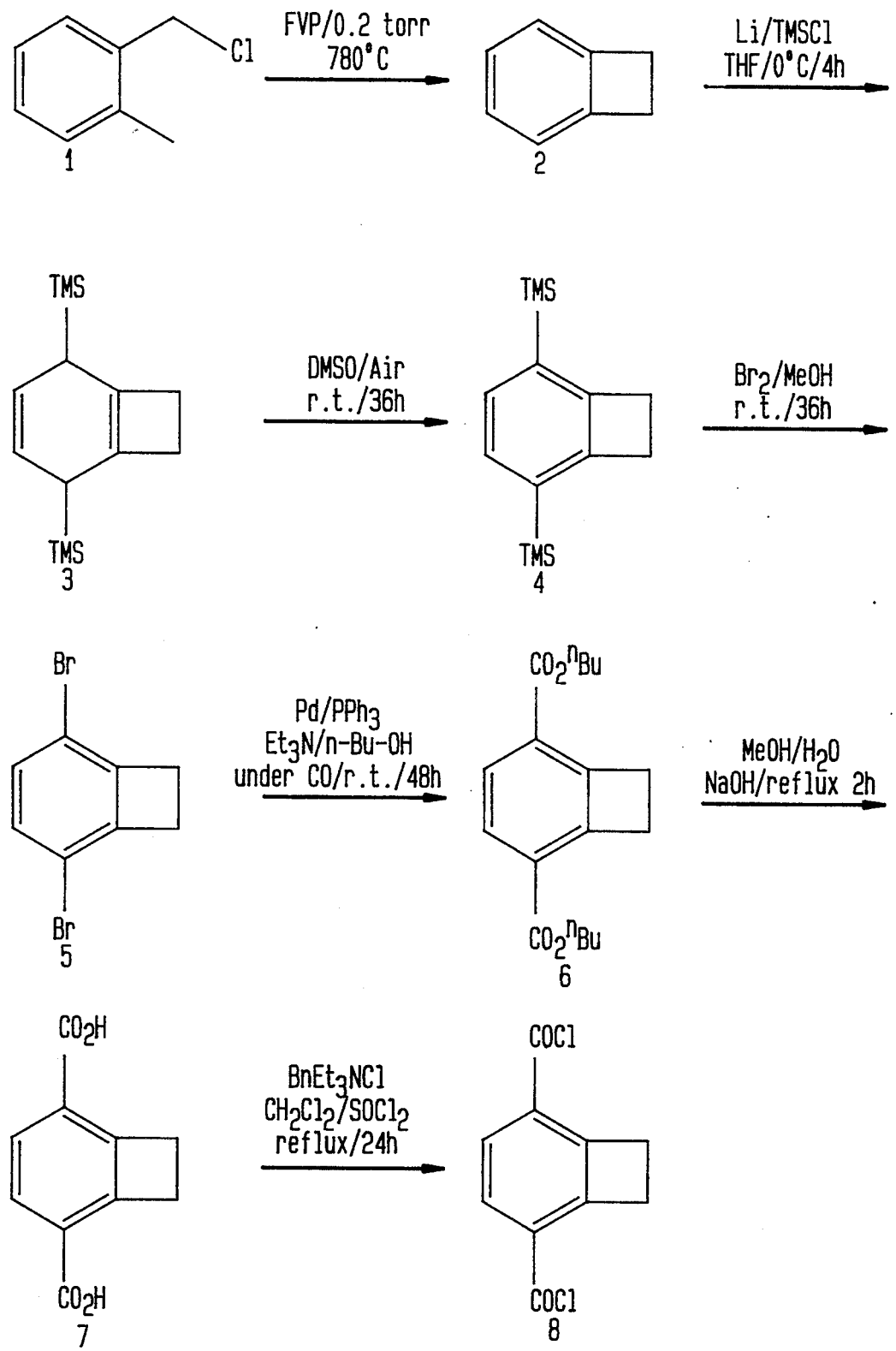
FIG. 1 is an illustrative preparatory scheme for 1,2-dihydrocyclobutabenzene-3,6-carboxylic acid and the corresponding diacid halide.

In a method embodiment of the invention, XTA and its corresponding acid halide are prepared in accordance with the illustrative preparatory scheme outlined in FIG. 1. This preparatory scheme is set forth to demonstrate one successful method of practicing the invention, and in no way is intended to limit the scope of the invention.

1,2-Dihydrocyclobutabenzene (BCB, compound 2)

The starting material, o-toluene-ethyl chloride, (compound 1, 10 g, 71.1 mmol) is degassed to 1 torr and the reaction is run by slow passage of α-chloro-o-xylene through a horizontal quartz tube containing no packing at 780° C. A Kugelrohl bulb in liquid nitrogen is placed at the oven outlet to collect the organic products followed by a second, more efficient trap to collect the HCl gas. This trap system utilizes the large difference in volatility of BCB and HCl to separate these species and thus simplify product workup. The reaction is run successfully over the pressure range of 200-500 mtorr and requires about 30 rain for 10 g of starting material. The crude product is taken up in 15% aqueous sodium hydroxide (200 ml) and extracted into pentane (3×200 ml). The entire procedure is repeated ten times. The combined organic layers are washed with saturated sodium chloride solution and analyzed by gas chromatography (GC) to be 88% BCB, 12% starting material, and <1% side reactions (styrene, ethyl benzene). Upon removing solvent, the oil is taken up in DMSO (1 L) with rapid stirring. Excess powdered KOH (20 g) is added to convert the α-chloro-o-xylene to α-hydroxy-o-xylene. This conversion is monitored by GC and is complete within 4 hours. The resulting solution is extracted into water (1 L), adjusted to pH 7, and washed with petroleum ether (3×750 ml). The combined organic layers are dried over anhydrous sodium sulfate and the organic solvent is removed. The resulting brown solution is distilled (65°-68° C. at 20 torr) to yield BCB (compound 2, 63 g, yield: 85%) as a colorless liquid.

3,6-Ditrimethylsilyl-1,2-Dihydrocyclobutabenzene (Compound 4)

A dry, magnetically stirred, 500 ml Schlenk flask is charged with a mixture of 57.2 g of lithium dispersion (5% sodium content) in mineral oil and placed under an argon atmosphere. Dry pentane is added via vacuum transfer under rapid stirring to solvate the mineral oil. The pentane/mineral oil solution is removed via filtration under argon. Pentane washing is repeated several times to ensure efficient removal of the mineral oil. The remaining mass of Li metal is determined (14.1 g, 2.03 mol) and the flask is cooled to 0° C. and charged with dry tetrahydrofuran (THF; 500 ml) via cannula transfer. In one portion, chlorotrimethylsilane (187.2 ml, 1.48 mol) is added. BCB (compound 2, 52 g, 500 mmol) is then added dropwise over a period of an hour via syringe to the rapidly stirring solution. The reaction continues for 4 hours and is monitored by GC until complete. Upon completion the mixture is cooled to 0° C. and isopropyl alcohol (100 ml) is added dropwise to carefully quench excess Li. The resulting solution is partitioned into water (1L) and washed with petroleum ether (3×750 ml). The combined organic layers are dried over anhydrous sodium sulfate and removal of solvent yields a brown oil (compound 3, 114.9 g, yield: 92%) that is a mixture of cis and trans isomers. The oil is placed in a 1 L three-neck flask, taken up in DMSO (750 ml), and bubbled with oxygen while the solution is rapidly stirred. Aromatization is complete in 24-36 hours as determined by GC. The resulting solution is taken up in water (1 L) and washed with petroleum ether (3×750 ml). The combined organic layers are dried over anhydrous sodium sulfate and, upon removal of solvent, yield crystals of 3,6-ditrimethylsilyl-1,2-dihydrocyclobutabenzene (compound 4, 109.2 g, yield: 88% based on BCB).

3,6-Dibromo-1,2-Dihydrocyclobutabenzene (Compound 5)

To a solution of compound 4 (100 g, 402 mmol) in methanol (2 L) is slowly added a solution of bromine (103.0 g, 625.8 mmol) in methanol (1 L). The addition takes place over 24 hours and the reaction is monitored by GC until complete (36 hours). The resulting solution is partitioned into water (1 L) and washed with petroleum ether (3×1 L). The combined organic layers are dried over anhydrous sodium sulfate. The solvent is removed to yield a yellow solid. The crude product is run through a short column of silica gel in petroleum ether:ethyl ether (90:10). Removal of eluent solvent yields white crystals of 3,6-dibromo-1,2-dihydrocyclobutabenzene (compound 5, 95 g, yield: 95%).

Dibutyl- 1,2-Dihydrocyclobutabenzene-3,6-Carboxylate (Compound 6)

A dry, magnetically stirred, 500 ml Schlenk flask is charged with compound 5 (40 g, 144 mmol), Pd(II) acetate (400 mg, 1.77 mmol), and triphenylphosphine (2.80 g, 10.6 mmol). The vessel is evacuated to 20 millitorr and refilled with carbon monoxide. This procedure is repeated four times. A solution of dry triethylamine (40 ml) and dry n-butanol (50 ml) is added via syringe. The resulting solution is degassed several times under rapid stirring to remove all gases dissolved in the solvents and the vessel is refilled with carbon monoxide. The contents of the vessel are then placed under a slight positive pressure with carbon monoxide and heated to 80° C. with very rapid stirring. The reaction requires about 48 hours and is monitored by GC until complete. The crude mixture is partitioned into water (1 L) and washed with petroleum ether (3×750 ml). The combined organic layers are dried over anhydrous sodium sulfate. The crude product is run through a short plug of silica gel with petroleum ether:ether (90:10) to remove catalyst. Removal of eluent solvent leaves a light yellow oil of dibutyl-1,2-dihydrocyclobutabenzene-3,6-carboxylate (compound 6, 40.60 g yield: 95%).

1,2-Dihydrocyclobutabenzene-3,6-Carboxylic Acid (Compound 7)

A solution of compound 6 (40 g, 142 mmol) and powdered sodium hydroxide (8 g, 200 mmol) is taken up in methanol (600 ml) with water (40 ml) and refluxed for two hours. Water (1 L) is added to dissolve excess sodium salts and the resulting solution is filtered. The mixture is then cooled to 0° C. and acidified to pH 7 to precipitate product. Filtration of the precipitated product and subsequent washing with acetone (300 ml) yields 1,2-dihydrocyclobutabenzene-3,6-carboxylic acid (XTA, compound 7, 26.5 g, yield: 97%) as a white powder.

In an alternative embodiment of the method (not shown on FIG. 1), compound 5 is converted to compound 7 by a Grignard reaction:

In a 300 ml round-bottom three-necked flask, fitted with a condenser, and equipped with a stirring bar, 0.950 g compound 5 and 2.00 g magnesium (Mg) are dried under reduced pressure. Dry ether (50 ml) is added to the flask under an inert ($N_2$) atmosphere. The reaction mixture is then heated to reflux. About 1 ml of dibromoethane is added to the reaction mixture to activate the surface of the Mg catalyst so that the reaction continues to reflux on its own. Additional dibromoethane (approximately 3.5 ml total in this example) is added as necessary to keep the reaction at reflux. The reaction progress is monitored by GC (the reactants have peaks at 2.45 and 5.44). When the product is the digrignard agent, $CO_2$ is bubbled through the reaction mixture. The reaction mixture is quenched with $H_2O$ (about 50 ml) and H+ (concentrated HCl, about 5 ml). The product diacid is extracted from the aqueous solution with 50:50 THF and ethyl acetate. The organic solvents are evaporated under reduced pressure to yield a yellow solid. The yellow solid is dissolved in 6 N NaOH and filtered through a glass frit. The basic solution is re-acidified with concentrated HCl to precipitate purified crystals of compound 7. (0.5 g; 74% yield).

1,2-Dihydrocyclobutabenzene-3,6-Acid Chloride (Compound 8)

To a dry, magnetically stirred, 1 L three-neck flask is added compound 7 (25.0 g, 130 mmol), benzyltriethylammonium chloride (65.0 mg, 0.29 mmol), and dry dichloromethane (600 ml). The mixture is brought to reflux and thionyl chloride (25.3 ml, 345 mmol) is added in one portion. The reaction requires about 24 hours and is monitored by GC until complete. The mixture is filtered hot and solvent is removed to yield dark yellow crystals which are sublimed (50 mtorr, 80° C.) to yield light yellow crystals. Recrystallization from dry ethyl ether yields white crystals of 1,2-dihydrocyclobutabenzene-3,6-acid chloride (compound 8, 28.6 g, yield: 96%).

Figure 2:
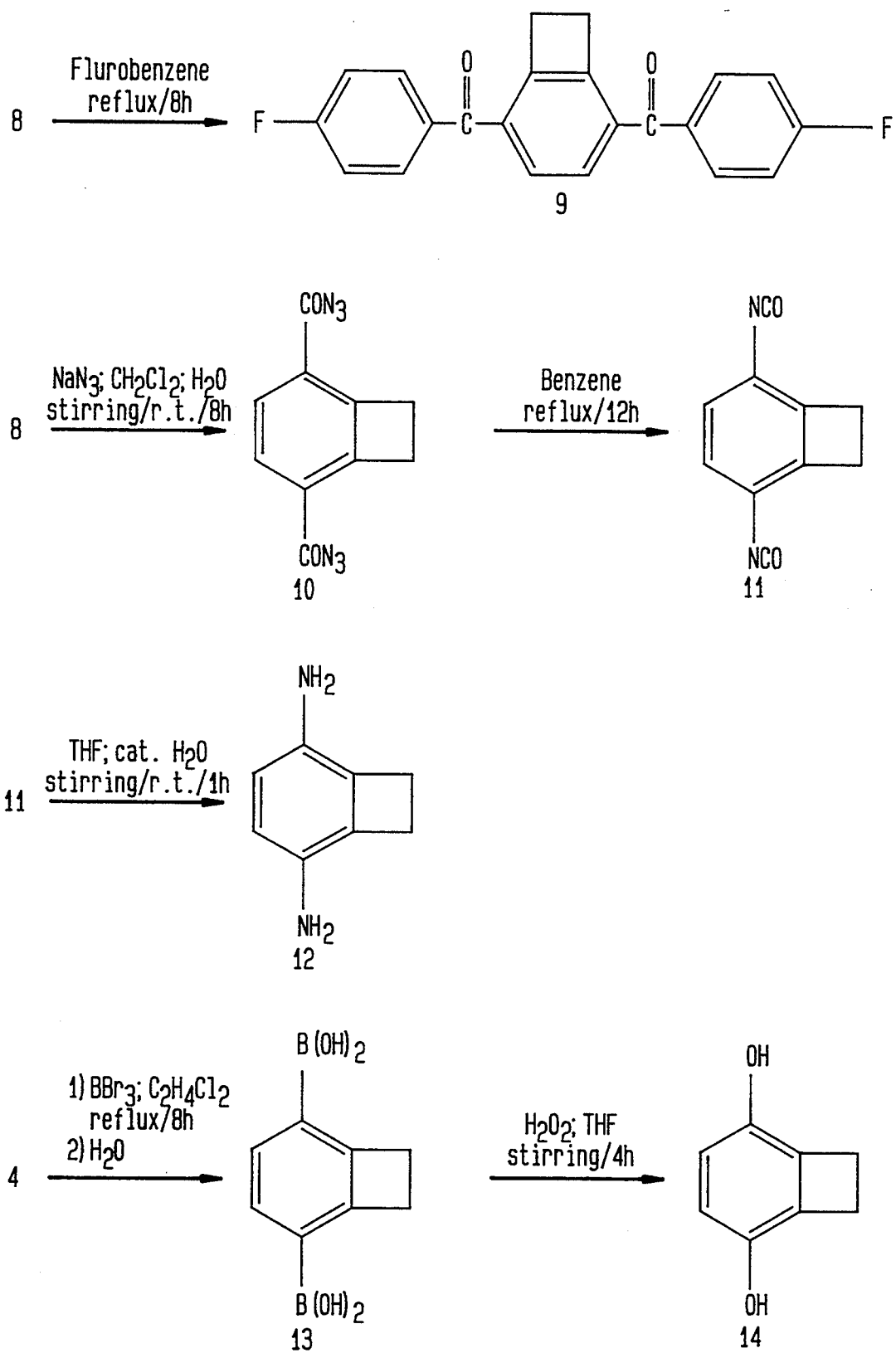
FIG. 2 and FIG. 3 show illustrative preparatory schemes for a series of cyclobutabenzene analogs within the contemplation of the present invention.
Figure 3:
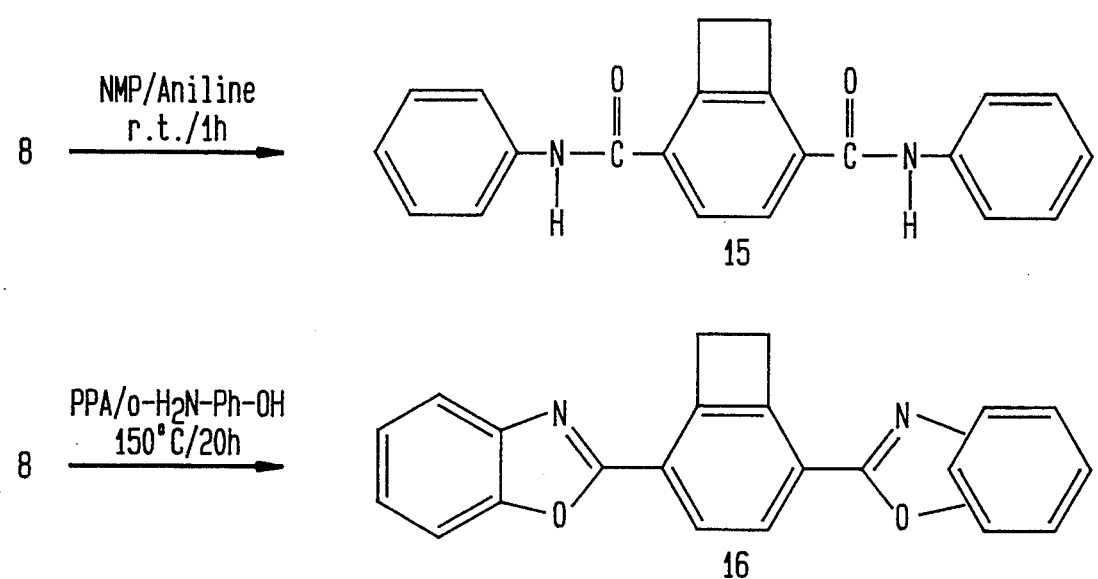

In additional illustrative embodiments of the invention, exemplary difunctionalized cyclobutabenzene analogs (Compounds 9 through 16) have been synthesized in accordance with the reaction schemes illustrated in FIGS. 2 and 3.

3,6-(4-Fluorobenzoyl)-1,2-Dihydrocyclobutabenzene (Compound 9)

Aluminum chloride (8.65 g, 65 mmol) is added to a solution of compound 8 (10.0 g, 44 mmol) in fluorobenzene (60 ml) in a three-neck, 250 ml flask fitted with a condenser, magnetic stirrer, and a nitrogen inlet. The mixture is refluxed for 12 hours and excess fluorobenzene is removed. The product is washed with 5% sodium hydroxide (100 ml), 5% HCl (100 ml), and water (100 ml) to yield light yellow crystals. Two recrystallizations from acetone yields white crystals of 3,6-(4-fluorobenzoyl)-1,2-dihydrocyclobutabenzene (compound 9, 13.8 g, yield: 90%).

1,2-Dihydrocyclobutabenzene-3,6-Isocyanate (Compound 11)

In a 500 ml round bottom flask, sodium azide (11.35 g, 175 mmol) is taken up in a suspension of water (200 ml) and dichloromethane (200 ml) under rapid stirring. Compound 8 (10.0 g, 44 mmol) is added in one portion. The reaction is monitored by GC until complete (4–6 hours). The resulting solution is extracted into water (100 ml) and washed with dichloromethane (3×150 ml). The combined organic layers are dried over anhydrous sodium sulfate and the solvent is removed to yield 1,2-dihydrocyclobutabenzene-3,6-acyl azide (compound 10, 9.7 g, yield: 92%) as white crystals. Compound 10 (9.0 g, 37 mmol) is taken up in dry benzene (250 ml) and refluxed under nitrogen for 12 hours The benzene is removed to yield light brown crystals. Recrystallization from dry ethyl ether yields white crystals of 1,2-dihydrocyclobutabenzene-3,6-isocyanate (compound 11, 6.4 g, yield: 93%).

1,2-Dihydrocyclobutabenzene-3,6-Diamine (Compound 12)

A solution of compound 11 (6.0 g, 32 mmol) in dry THF (40 ml) is added dropwise to a solution of concentrated hydrochloric acid (20 ml) and THF (60 ml) over a period of 30 minutes with stirring. The reaction is allowed to proceed with stirring at room temperature for about an hour during which the amine-hydrochloride salt precipitates from solution. THF and excess HCl are removed under reduced pressure to yield white crystals of 1,2-dihydrocyclobutabenzene-3,6-diamine (compound 12, 6.4 g, yield: 93%) as the hydrochloride salt.

3,6-Hydroxy-1,2-Dihydrocyclobutabenzene (Compound 14)

In a three-neck, 250 ml flask fitted with a condenser, magnetic stirrer, and a nitrogen inlet, boron tribromide (15.0 g, 60 mmol) is added to a solution of compound 4 (5.0 g, 20 mmol) in dry dichloroethane (150 ml). The reaction mixture is brought to reflux and requires about 12 hours for completion. The mixture is taken up in water (300 ml) and washed with ethyl acetate (3×200 ml). The combined organic layers are dried over anhydrous sodium sulfate. Removal of solvent yields a brown solid which is taken up in 6N sodium hydroxide (100 ml) and filtered to remove organic impurities. Acidification of the filtrate to pH 7 and filtration of the resulting precipitate yields 1,2-dihydrocyclobutabenzene-3,6-boronic acid (compound 13, 3.2 g, yield: 83%) as a white powder.

Compound 13 (1.0 g, 5 mmol) is added to a solution of diethyl ether (100 ml) and 30% hydrogen peroxide under rapid stirring at room temperature. The reaction is complete in 4 hours. Excess peroxide is quenched with 10% ferrous ammonium sulfate. The solution is brought to pH 7 and extracted with diethyl ether (3×100 ml). The combined organic layers are dried over anhydrous sodium sulfate. Removal of solvent yields 3,6-hydroxy-1,2-dihydrocyclobutabenzene (compound 14, 1.47 g, yield: 65%) as a yellow oil.

1,2-Dihydrocyclobutabenzene-3,6-Benzamide (Compound 15)

A 100 ml, magnetically stirred, round bottom flask is charged with aniline (1.63 g, 17.2 mmol) and N-methyl-l-pyrrolidinone (5 ml). Compound 8 (1.0 g, 4.4 mmol) is added with stirring. A yellow solution results. The reaction is complete within about one hour. The solution is filtered to produce yellow crystals which are washed with water (50 ml) and acetone (50 ml) to yield white crystals of 1,2-dihydrocyclobutabenzene-3,6-benzamide (compound 15, 1.45 g, yield: 97%).

1,2-Dihydrocyclobutabenzene-3,6-Benzoxazole (Compound 16)

A 250 ml-three neck flask equipped with a mechanical stirrer and a nitrogen inlet is charged with compound 8 (1.0 g, 4.4 mmol), degassed polyphosphoric acid (50 ml), and 2-aminophenol (1.9 g, 17.4 mmol). The reaction is heated to 90° C. with stirring and degassed to remove HCl. The reaction mixture is then heated to 150° C. for 20 hr. The resulting solution is partitioned into water (500 ml), brought to neutral pH conditions via addition of sodium hydroxide solution, and filtered to collect the solid. Recrystallization of the solid material from dimethyl sulfoxide yields fluffy, pale yellow crystals of 1,2-dihydrocyclobutabenzene-3,6-benzoxazole (compound 16, 1.19 g, yield: 80%).

To explore the thermal behavior of the two model XTA compounds related to the known high-performance polymers PPTA (compound 15) and PZBO (compound 16), differential scanning calorimetry (DSC) experiments were conducted. The results are reported on Table 1 and reveal a reversible melting followed by an irreversible chemical reaction. This reaction, presumably the opening of the cyclobutane ting, proceeds appreciably above 300° C. Both compounds are stable under the synthesis and processing conditions described hereinabove.

TABLE 1

| DSC data of 1,2-Dihydrocyclobutabenzene Model Compounds 15 and 16 | | | |
|---|---|---|---|
| Compound | Molecular Formula | $T_m{}^a$ | $T_r{}^b$ |
| 15 | $C_{21}H_{18}N_2O_2$ (330.1) | 314° C. | 335° C. |
| 16 | $C_{22}H_{14}N_2O_2$ (338.4) | 303° C. | 349° C. |

Figure 4:
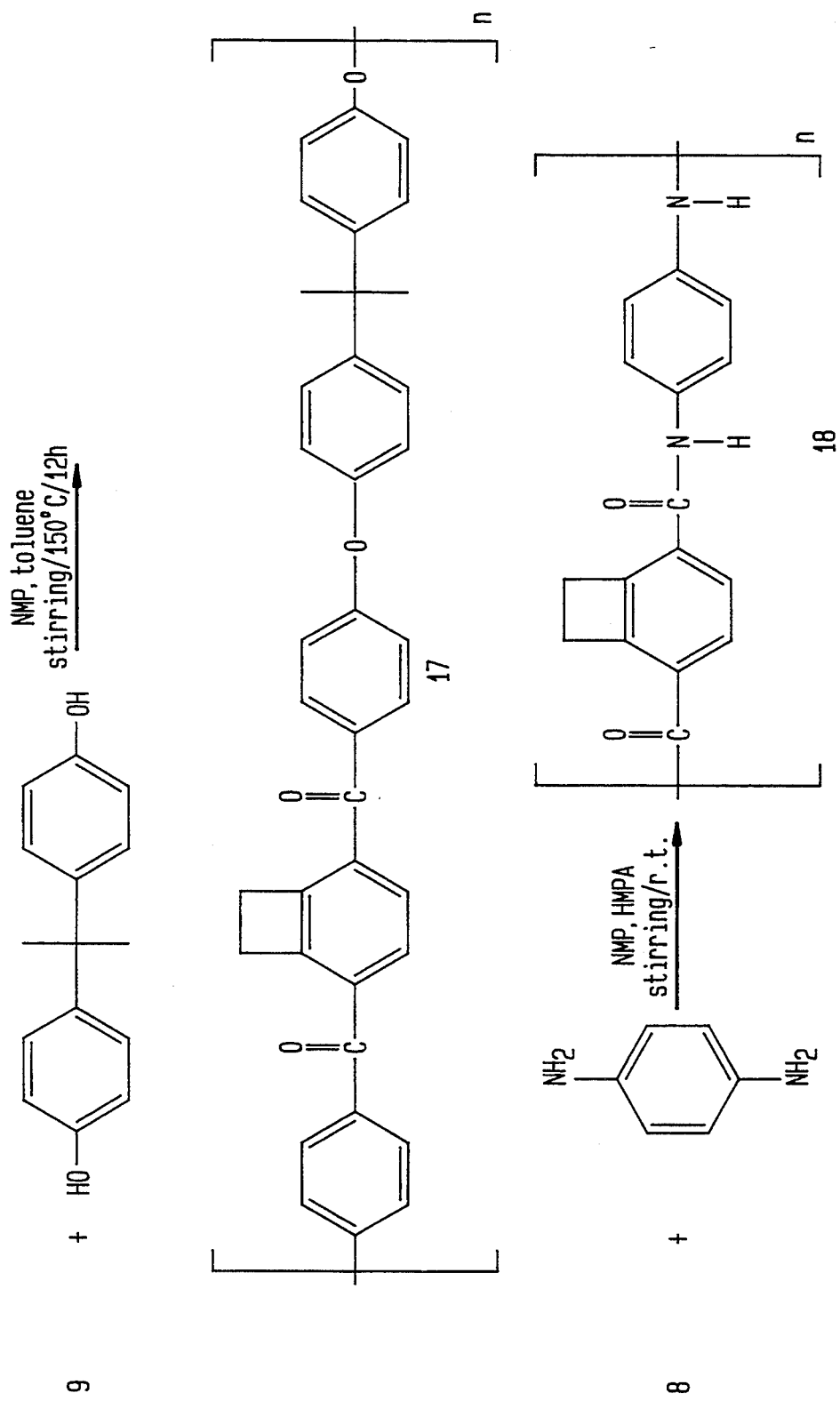
FIG. 4 shows illustrative preparatory schemes for two resins prepared with the difunctionalized cyclobutabenzene monomers of the present invention, in particular, a poly(paraphenylene diamine terephthalate) and a poly(ether ether ketone ketone)

$^aT_m$ - reversible melting transition (heating rate = 20° C./min)
$^bT_r$ - onset of irreversible chemical reaction In a further specific embodiments of the invention, resins have been formed by polymerization of the cyclobutabenzene monomers of the present invention with copolymers which are capable of reacting with the X/Y-functionalities of the cyclobutabenzene monomer. FIG. 4 shows illustrative preparatory schemes for two such illustrative resins.

Poly(Ether Ether Ketone Ketone) (Compound 17, PEEKK-BCB)

To a flask equipped with a magnetic stirrer, a Dean-Stark trap, and a nitrogen inlet is added compound 9 (2.0901 g, 6 mmol), 4,4'-isopropylidenediphenol (1.37 g, 6 mmol), dry potassium carbonate (1.74 g, 12.6 mmol), dry N-methyl-1-pyrrolidinone (NMP, 16 ml), and dry toluene (12 ml). The reaction mixture is heated to 140° C. with stirring for 3 hours to dehydrate the reaction and remove the toluene. After removal of toluene, the reaction is stirred for another 3 hours at 140° C. The mixture is then precipitated into water and the polymer is washed with acetone and dried at 60° C. under vacuum for 24 hours to yield the poly(ether ether ketone ketone), compound 17 (3.16 g, yield: 98% ).

Comparative DSC studies were conducted with poly(ether ether ketone ketone) polymers to determine the effect of crosslinking. Poly(ether ether ketone ketone) polymers were synthesized without the BCB function and with the BCB function (compound 17).

Referring to Table 2, the PEEKK without BCB showed a reversible melt at 155° C. and decomposed at 405° C. (Run #1). PEEKK-BCB exhibited a similar melt at 158° C., but also an irreversible reaction at 305° C. The heating was stopped at 350° C. and cooled to 50° C. to avoid decomposition (Run #2). The same PEEKK-BCB sample was again heated and no melt or reaction was observed until decomposition at 410° C. (Run #3). Table 2 shows that decomposition temperature is not greatly increased by adding the BCB functionality. However, once crosslinked, PEEKK-BCB does not melt. This characteristic extends its mechanical usefulness safely to about 350° C. In contrast, PEEKK without the BCB functionality melts at 150° C., thereby losing its mechanical usefulness at a much lower temperature.

TABLE 2

| | DSC data of PEEKK polymers | | | |
|---|---|---|---|---|
| Compound | Run # | $T_m{}^a$ | $T_r{}^b$ | $T_d{}^c$ |
| PEEKK | 1 | 150° C. | — | 405° C. |
| PEEKK-BCB | 2 | 158° C. | 305° C. | — |
| | 3 | — | — | 410° C. |

$^aT_m$ - reversible melting transition (heating rate = 20° C./min)
$^bT_r$ - onset of irreversible chemical reaction
$^cT_d$ - onset of irreversible chemical decomposition Poly(paraphenyl Diamine Terephthalate) Copolymerized With XTA (Compound 18, PPTA-co XTA)

XTA is incorporated into the backbone of a polyamide related to poly(paraphenylene diamine terephthalate). The resulting polymer is herein designated PPTA-co-XTA.

To a flask equipped with a magnetic stirrer and a nitrogen inlet is added para-phenylene diamine (1.0814 g, 10 mmol), N-methyl-l-pyrrolidinone (NMP, 13.4 ml), and hexamethylphosphoramide (HMPA, 26.8 ml). At room temperature, under very rapid stirring, compound 8 (2.2906 g, 10 mmol) is added in one portion. The reaction mixture is rapidly stirred for 15 minutes and then allowed to stand for 10 hours. The polymer is precipitated in 2N sodium hydroxide, washed with acetone, and dried under vacuum overnight to yield the PPTA-co-XTA compound 18 (2.5 g, yield: 95%).

This procedure was repeated using varying molar ratios of TA:XTA in the polymerization reaction to show the ability of XTA to be used as a comonomer with TA in polymer synthesis. The ratio of TA:XTA and the subsequent intrinsic viscosities of the resulting PPTA-based polymer are shown in Table 3. Table 3 reports the intrinsic viscosity (in dL/g) of the polymer in 100% sulfuric acid as measured in an Ubbelodhe capillary tube at 30° C. Table 3 demonstrates that XTA can be incorporated successfully into current polymer synthesis techniques to yield a high molecular weight polymer.

TABLE 3

Molar ratio and intrinsic viscosity of copolymers based on PPTA

| mmol diamine | mmol TA | mmol XTA | intrinsic viscosity |
|---|---|---|---|
| 10 | 0 | 10 | 5.7 |
| 10 | 5.0 | 5.0 | 6.6 |
| 10 | 7.5 | 2.5 | 4.9 |
| 10 | 9.0 | 1.0 | 5.3 |
| 10 | 9.5 | 0.5 | 5.8 |
| 10 | 10 | 0 | 5.5 |

Figure 5:
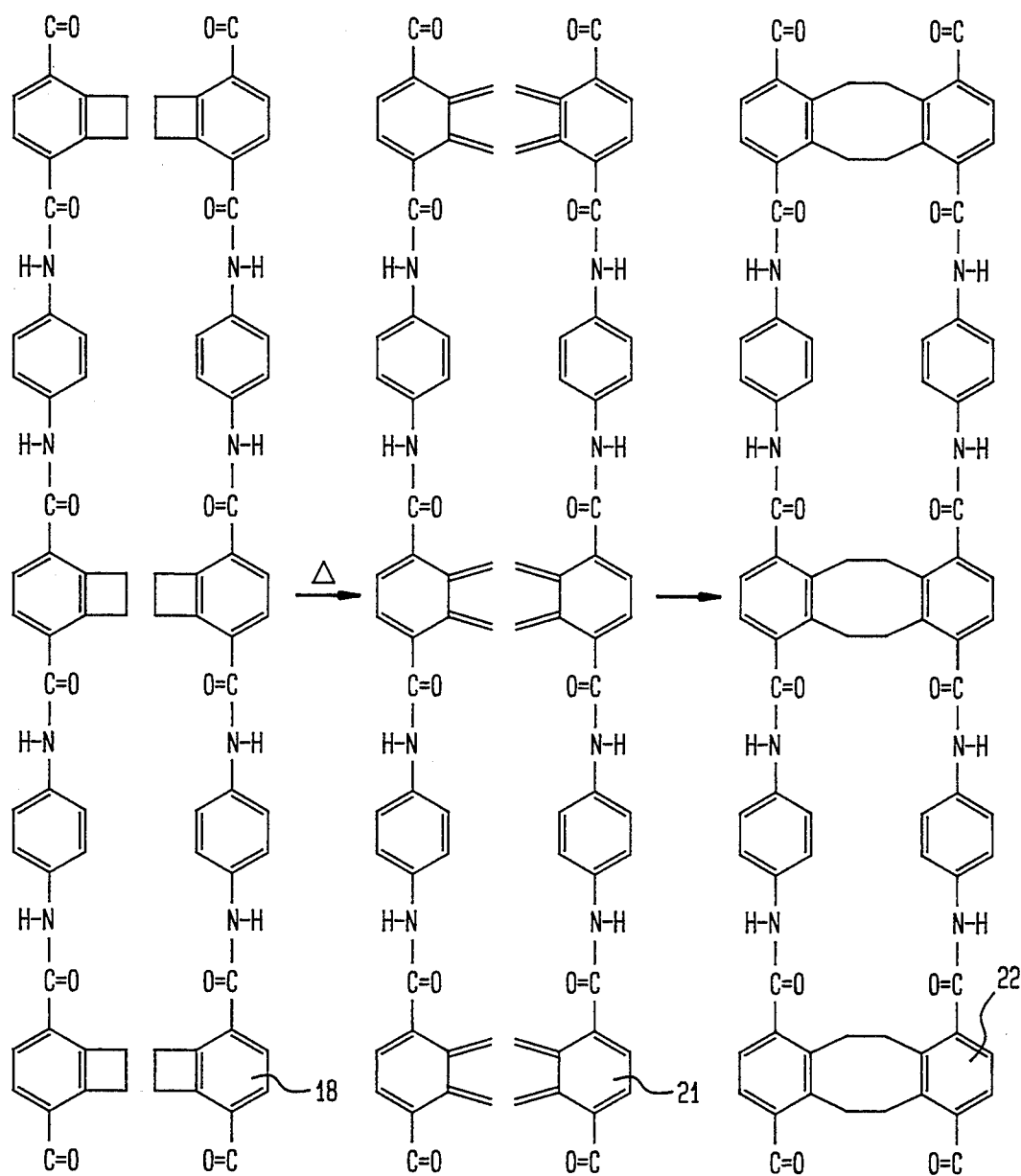
FIG. 5 is molecular structure depiction of a resin having cyclobutabenzene incorporated into a polymer backbone of the type comprising a polyamide, specifically a poly(paraphenylene diamine terephthalate), and the consequent structure of the improved polymer after crosslinking through the cyclobutane functionalities.

Referring to FIG. 5, the BCB-containing polymer, compound 18, can be chemically crosslinked by subjecting the resin to a temperature in excess of 300° C. to open the cyclobutane ring to form the highly reactive intermediate (o-quinodimethane) 21 which reacts with other open rings to form a highly crosslinked three-dimensional polymer network 22.

Incorporating the cyclobutabenzene functionality into the polymer backbone has unique advantages over the prior art polymerization techniques. First, the BCB monomers of the present invention can be incorporated into the polymer backbone in any amount that is required to achieve a desired property. Second, crosslinking is rapid and can be performed before, during, or after fiber spinning or casting of films. This eliminates the problem of disrupting crystallinity. Crosslinking can be easily achieved by heating the product to a temperature in excess of 300° C. and no catalysts are required for initiation. Furthermore, no volatile byproducts are released during the crosslinking reaction, which is accompanied by a minimal change in volume. These advantageous characteristics enable the high orientation and order that exists in the known high-performance polymers to be retained.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A monomer of the general formula:

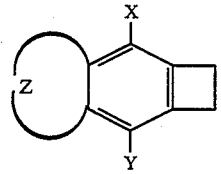

wherein Z is hydrogens or a cyclobutane ring; and X and Y are carboxyl, amino, isocyanate, acid halide, or 4-fluorobenzoyl groups.

2. The monomer of claim 1 which is 1,2-dihydrocyclobutabenzene-3,6-carboxylic acid.

3. The monomer of claim 1 which is 1,2-dihydrocyclobutabenzene-3,6-diamine.

4. The monomer of claim 1 which is 1,2-dihydrocyclobutabenzene-3,6-isocyanate.

5. The monomer of claim 1 which is 1,2-dihydrocyclobutabenzene-3,6-acid halide.

6. The monomer of claim 1 which is 3,6-(4-fluorobenzoyl)-1,2-dihydrocyclobutabenzene.

* * * * *